(12) United States Patent  
Suprono et al.

(10) Patent No.: US 11,080,554 B2  
(45) Date of Patent: Aug. 3, 2021

(54) METHODS AND SYSTEMS FOR IMPLANT IDENTIFICATION USING IMAGING DATA

(71) Applicant: LOMA LINDA UNIVERSITY, Loma Linda, CA (US)

(72) Inventors: Montry Suprono, Loma Linda, CA (US); Robert Walter, Loma Linda, CA (US)

(73) Assignee: LOMA LINDA UNIVERSITY, Loma Linda, CA (US)

( * ) Notice: Subject to any disclaimer, the term of this patent is extended or adjusted under 35 U.S.C. 154(b) by 170 days.

(21) Appl. No.: 16/466,681

(22) PCT Filed: Dec. 19, 2017

(86) PCT No.: PCT/US2017/067316  
§ 371 (c)(1),  
(2) Date: Jun. 5, 2019

(87) PCT Pub. No.: WO2018/118919  
PCT Pub. Date: Jun. 28, 2018

(65) Prior Publication Data  
US 2019/0303712 A1 Oct. 3, 2019

Related U.S. Application Data

(60) Provisional application No. 62/436,324, filed on Dec. 19, 2016.

(51) Int. Cl.  
*G06K 9/00* (2006.01)  
*G06K 9/62* (2006.01)  
(Continued)

(52) U.S. Cl.  
CPC ............ *G06K 9/6215* (2013.01); *A61B 6/14* (2013.01); *A61C 8/00* (2013.01); *B25J 9/16* (2013.01);  
(Continued)

(58) Field of Classification Search  
CPC ............ G06K 9/6215; G06K 9/00624; G06K 9/3208; G06K 9/6255; G06K 9/6262;  
(Continued)

(56) References Cited

U.S. PATENT DOCUMENTS 8,170,327 B2 * 5/2012 Glor .................... A61C 13/0004  
382/154  
8,249,318 B2 * 8/2012 Schmitt ................ G06K 9/6276  
382/128

(Continued)

OTHER PUBLICATIONS

International Search Report and Written Opinion for PCT/US17/67316, dated Mar. 7, 2018.

*Primary Examiner* — Gregory M Desire  
(74) *Attorney, Agent, or Firm* — Womble Bond Dickinson (US) LLP

(57) ABSTRACT

Embodiments provide techniques, including systems and methods, for processing imaging data to identify an installed component. Embodiments include a component identification system that is configured to receive imaging data including an installed component, extract features of the installed component from the imaging data, and search a data store of components for matching reference components that match those features. A relevance score may be determined for each of the reference components based on a similarity between the image and a plurality of reference images in a component model of each of the plurality of reference components. At least one matching reference component may be identified by comparing each relevance score to a threshold relevance score and matching component information may be provided to an end-user for each matching reference component.

18 Claims, 10 Drawing Sheets

(51) Int. Cl.
   *A61B 6/14* (2006.01)
   *A61C 8/00* (2006.01)
   *G06T 7/00* (2017.01)
   *B25J 9/16* (2006.01)
   *G06K 9/32* (2006.01)

(52) U.S. Cl.
   CPC ....... *G06K 9/00624* (2013.01); *G06K 9/3208* (2013.01); *G06K 9/6255* (2013.01); *G06K 9/6262* (2013.01); *G06T 7/0014* (2013.01); *G06K 9/6201* (2013.01); *G06T 2207/10116* (2013.01); *G06T 2207/30036* (2013.01)

(58) Field of Classification Search
   CPC . G06K 9/6201; A61B 6/14; A61C 8/00; B25J 9/16; G06T 2207/10116; G06T 2207/30036; G06T 7/0014
   See application file for complete search history.

(56) References Cited

U.S. PATENT DOCUMENTS

| | | | |
|---|---|---|---|
| 8,582,870 B2* | 11/2013 | Glor | A61C 13/0004 382/154 |
| 9,031,284 B2* | 5/2015 | Spath | G06T 7/70 382/103 |
| 10,426,578 B2* | 10/2019 | Rubbert | A61C 13/0028 |
| 2007/0127822 A1 | 6/2007 | Boose | |
| 2008/0004517 A1* | 1/2008 | Bhandarkar | G06T 7/33 600/407 |
| 2011/0305376 A1 | 12/2011 | Neff | |
| 2014/0066937 A1 | 3/2014 | Wiebe, III et al. | |
| 2014/0185865 A1 | 7/2014 | Spath | |
| 2014/0371911 A1 | 12/2014 | Mian et al. | |
| 2016/0207203 A1 | 7/2016 | Mian et al. | |
| 2017/0340418 A1* | 11/2017 | Raanan | G06K 9/228 |
| 2019/0303712 A1* | 10/2019 | Suprono | G06K 9/6215 |

* cited by examiner

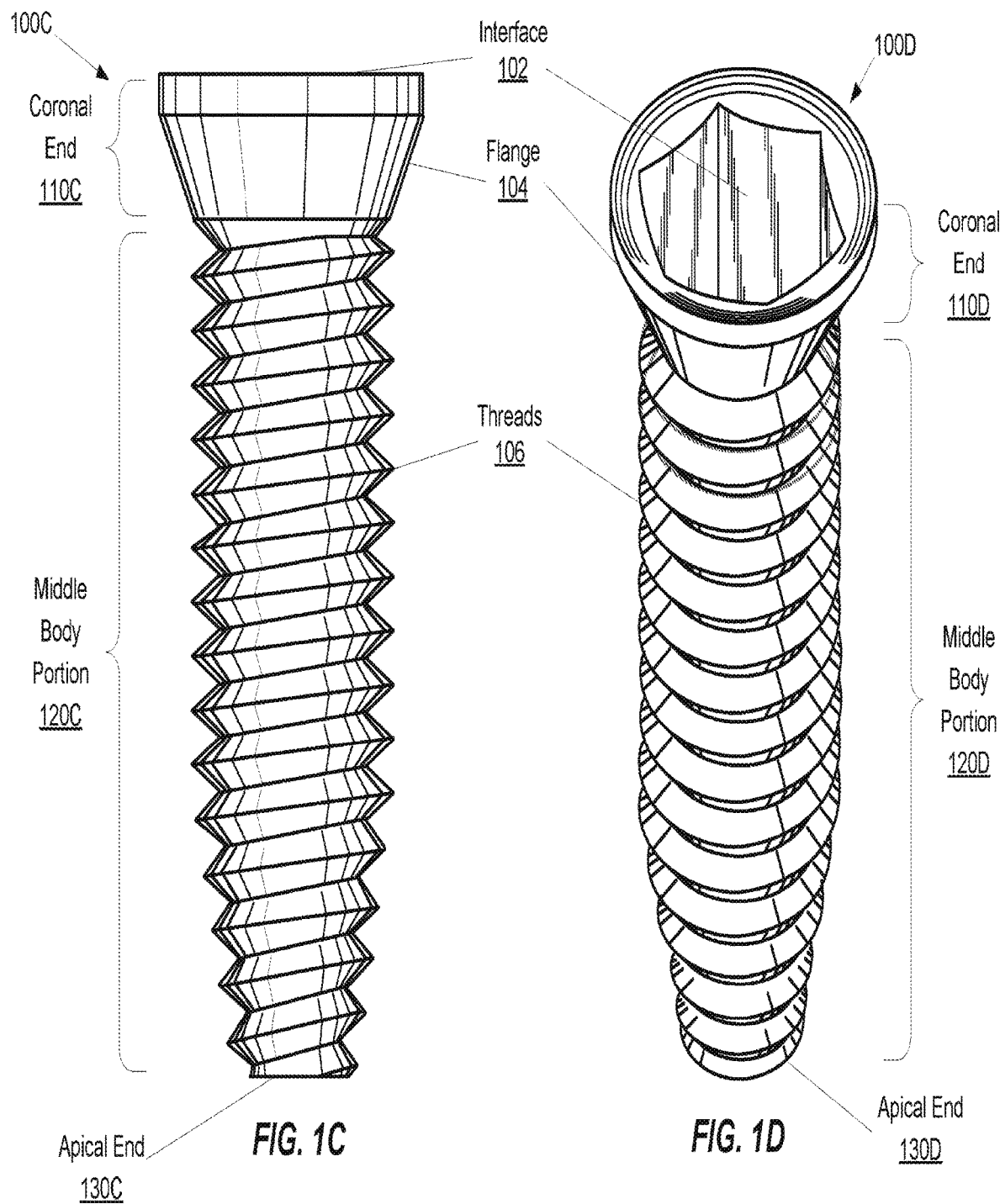

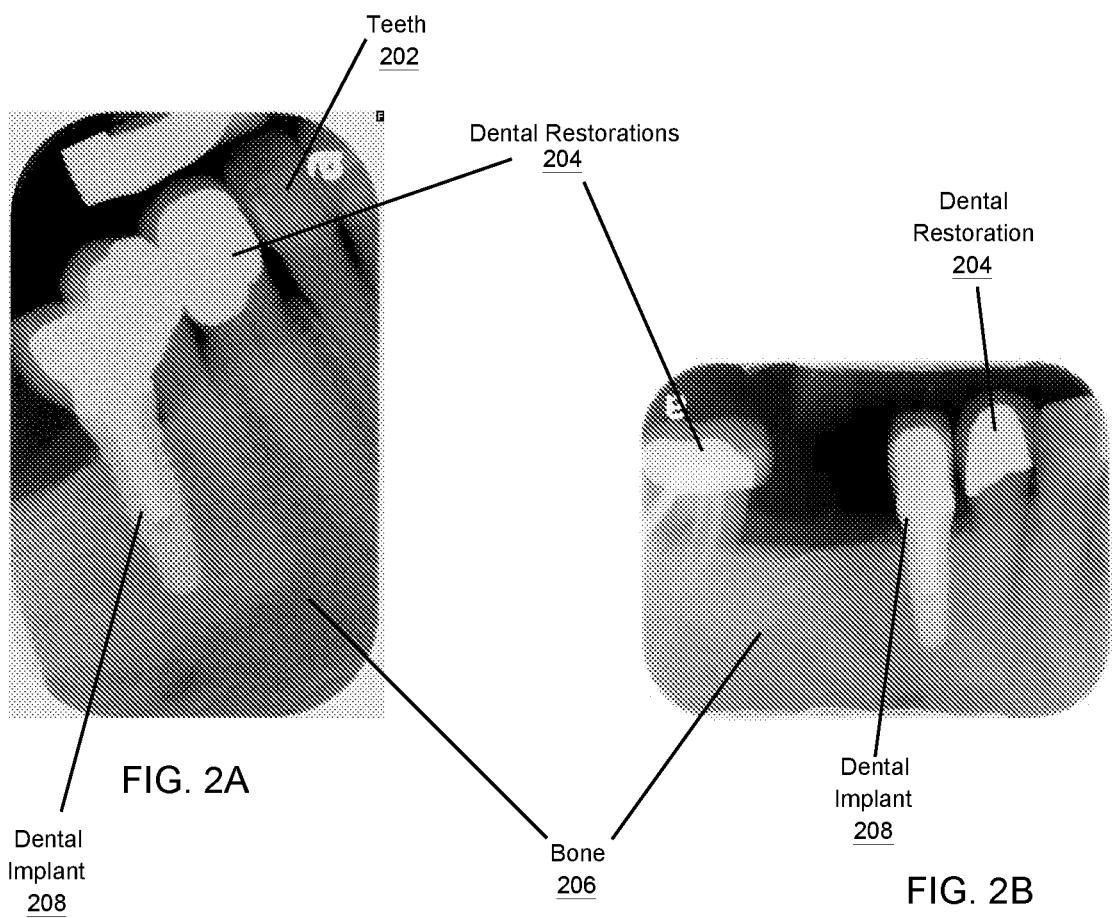

METHODS AND SYSTEMS FOR IMPLANT IDENTIFICATION USING IMAGING DATA

CROSS-REFERENCE TO RELATED APPLICATIONS

This application is a U.S. National Phase Under 35 U.S.C. § 371 of International Application No. PCT/US17/67316, titled "METHODS AND SYSTEMS FOR IMPLANT IDENTIFICATION USING IMAGING DATA," filed Dec. 19, 2017, which is a PCT application claiming priority to and the benefit of U.S. Provisional Application No. 62/436,324, titled "METHODS AND SYSTEMS FOR IMPLANT IDENTIFICATION USING IMAGING DATA," filed Dec. 19, 2016, which is incorporated herein in its entirety by reference.

BACKGROUND

It can be difficult to identify dental implants from X-rays due to the limited viewpoints of the implant that can be captured when the implant is installed in a patient. While two dimensional radiographs can be taken of the dental implants, distinguishing features that allow the implants to be identified may not be captured, or it may be difficult, inefficient, and time intensive to consistently capture the correct orientation of the implant installed in the patient. As such, many times a conclusive match cannot be made and in some instances an implant cannot successfully be identified.

BRIEF DESCRIPTION OF THE DRAWINGS

Various embodiments in accordance with the present disclosure will be described with reference to the drawings, in which:

FIGS. 1A-1D illustrate example images of different orientations of two different reference components, in accordance with an embodiment of the present invention;

FIGS. 2A-2D illustrate example images from different orientations showing different installed components for identification, in accordance with an embodiment of the present invention;

DETAILED DESCRIPTION

Figures 1A, 1B:
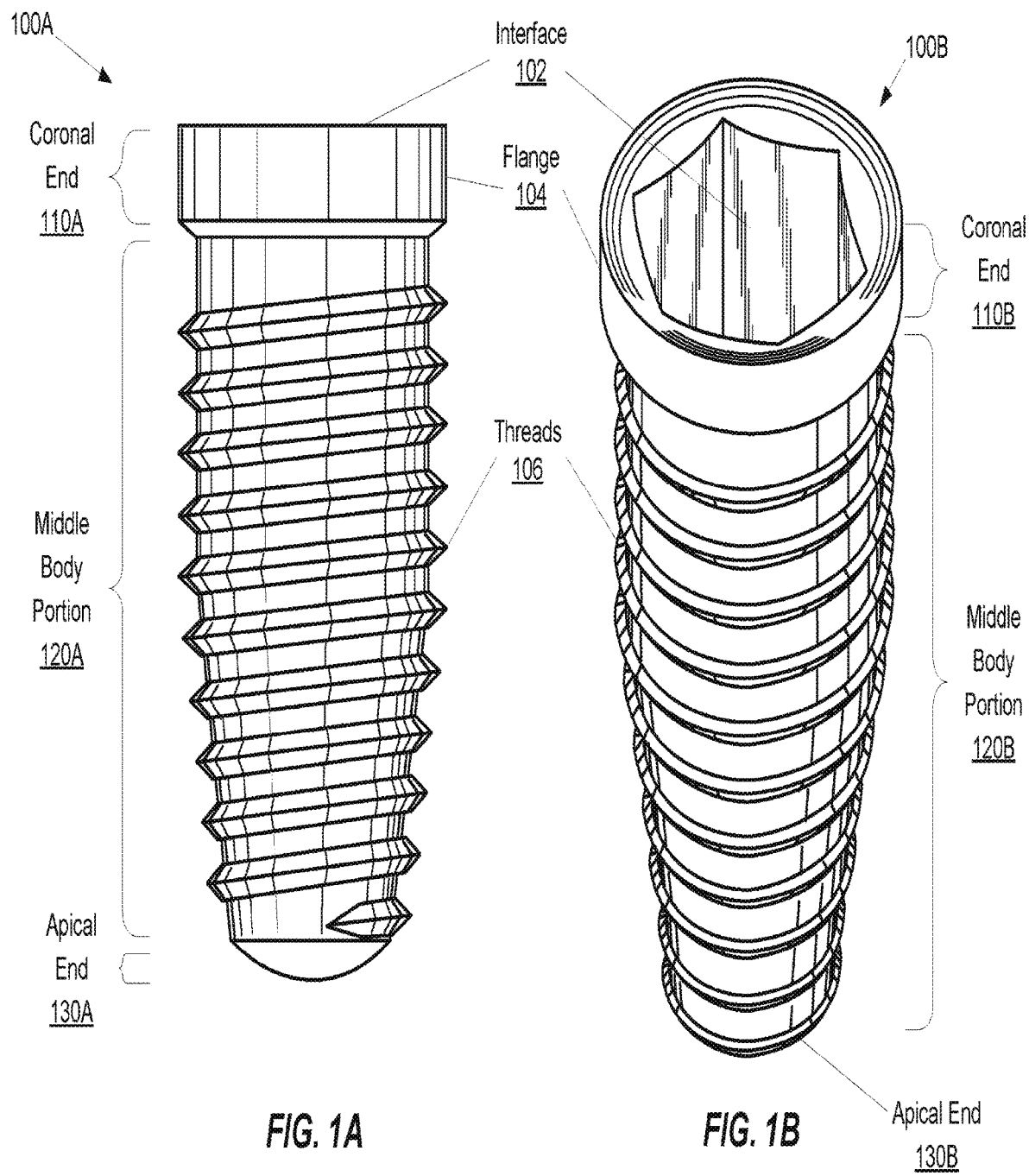

In the following description, various embodiments will be described. For purposes of explanation, specific configurations and details are set forth in order to provide a thorough understanding of the embodiments. It will also be apparent to one skilled in the art, however, that the embodiments may be practiced without the specific details. Furthermore, well-known features may be omitted or simplified in order not to obscure the embodiment being described.

As illustrated in FIGS. 1-8, and as further described herein, embodiments provide techniques, including systems and methods, for processing imaging data including an installed component to identify the corresponding component captured in the image. Embodiments include a component identification system that is configured to receive imaging data including an installed component, extract features of the installed component from the imaging data, and search a data store of components for matching reference components that match those features. A relevance score may be determined for each of the reference components based on a similarity between the image and a plurality of reference images in a component model of each of the plurality of reference components. At least one matching reference component may be identified by comparing each relevance score to a threshold relevance score and matching component information may be provided to an end-user for each matching reference component.

Accordingly, embodiments use image feature extraction and image matching to allow for efficient capture and identification of installed implants. Some embodiments may use component models that can be used to match installed components using imaging data capturing the implants at a variety of angles and orientations. As such, a two dimensional image of a dental implant taken at any angulation may be identified, leading to easier imaging capture of installed implants, fewer x-rays that expose patients to radiation, as well as savings in time by a surgeon or other service provider to identify a matching implant. The component models may be provided from manufacturers and/or may be generated using a variety of previously classified images of implants. Accordingly, using the imaging-based component models, components from imaging data may be quickly and efficiently identified from a wide range of orientations that may otherwise be difficult to identify and/or differentiate.

Moreover, by limiting the comparison of imaging models to those reference components that match features extracted from the imaging data, embodiments provide a more efficient and faster comparison process that limits the amount of system resources expended to identify matching components. Image comparison processing is time and resource intensive. Thus, by limiting the number of component models that are mapped and/or compared to the imaging data, the system can more efficiently identify the component from the imaging data. As such, the system identifies those reference components that could be a potential match to the installed component from the imaging data before mapping and/or performing image comparison to a component model. This conserves system resources and increases the speed of the component identification process.

Dental implants come in a wide-variety of different shapes and sizes and have a variety of different features associated with them depending on their specific design, the purpose of the implant, the manufacture date, the material, etc. For example, FIGS. 1A-1D illustrate different orientations of two different dental implant components. As can be seen in FIGS. 1A-1D, the components include a variety of different widths, lengths, shapes, designs, and other features. For example, there are over 400 dental implant companies making a variety of different shapes and sizes of dental hardware. These different types of dental hardware can include different features such as a length of the component, a width of the component, a type of interface of the component, a type of flange of the component, presence of micro-threading on a coronal end of the component, a presence of a collar on the coronal end of the component, a type of taper of a body of the component, a presence of threading on the body of the component, a type of the threading on the body of the component, a presence of grooves in the body of the component, a shape of an apex end of the component, a presence of an open apex end of the component, a shape of the body of the component, a shape of apertures within the apex end of the component, a presence of a chamber in the apex end of the component, and a presence of grooves within the apex end of the component. FIGS. 1A and 1B show different views of a first kind of dental implant from different orientations. FIGS. 1C-1D show different views of a second kind of dental implant from the same two orientations as FIGS. 1A and 1B. While FIGS. 1A and 1B show only two different orientations of a reference component model, a full reference component model may have many more orientation viewpoints showing any possible point of view, elevation, and perspective of a dental implant. Additionally, although not shown in FIGS. 1A-1D, the internal mechanisms and components of the dental hardware may be shown in different orientations such that the internal features of the implants may be incorporated into the reference component models as well. Additionally, although FIGS. 1A-1D show views of the reference components, in other embodiments, these views may be radiographs of the reference components. In some embodiments these reference images may be of installed components and in other embodiments, the reference images may be of uninstalled or free-standing components.

For example, as shown in FIGS. 1A and 1B, multiple views 100A and 100B of a dental implant component are shown. The dental implant component may include various portions, including a coronal end 110A and 110B, including an interface 102 and flange 104, a mid-body portion 120A, 120B, including threads 106, and an apical end 130A, 130B. The dental implant component may include an interface 102 at coronal end 110A. Similarly, as shown in FIGS. 1C and 1D, multiple views 100C and 100D of a different dental implant component are shown. The dental implant component may include various portions, including a coronal end 110C and 110D, including an interface 102 and flange 104, a mid-body portion 120C, 120D, including threads 106, and an apical end 130C, 130D.

In practice, it can be difficult to identify particular implants (also referred to as components) from radiographs (e.g., X-ray images or "X-rays") due to the wide-variety of different implants available on the market. For example, FIGS. 2A-2D and 3 illustrate example X-ray imaging data of installed components from multiple orientations, in accordance with an embodiment of the present invention. Additionally, it can be difficult to obtain radiographs from the correct angle to show distinguishing features or to match preferred views of such dental implants. For example, as can be seen from FIGS. 2A-2D and 3, the orientations of the installed components shown in the radiographs are not the same as the reference components in FIGS. 1A-1D. This can lead to problems with identifying matching features between images of reference components and images of installed components or different orientation viewpoints of installed components.

Accordingly, embodiments are directed to providing a system that can identify components using data stores of component features, reference images of components, reference component models, and image processing and comparison capabilities to identify appropriate matching components to an installed implant. Three dimensional structural analysis and imaging of dental implants may be collected for the data store with site specific markers on the implant threads, grooves, platform, and apex that may map the dental implants to a component model. The component model may include hundreds or thousands of different images of the reference component from a variety of different orientations to allow for the closest possible match of the reference component to received image data for comparison of features. Image feature extraction may be used to analyze two dimensional radiographic images and correlate the specific markers to the specific type and manufacturer of dental implants in any vertical and horizontal position.

Figures 2C, 2D:
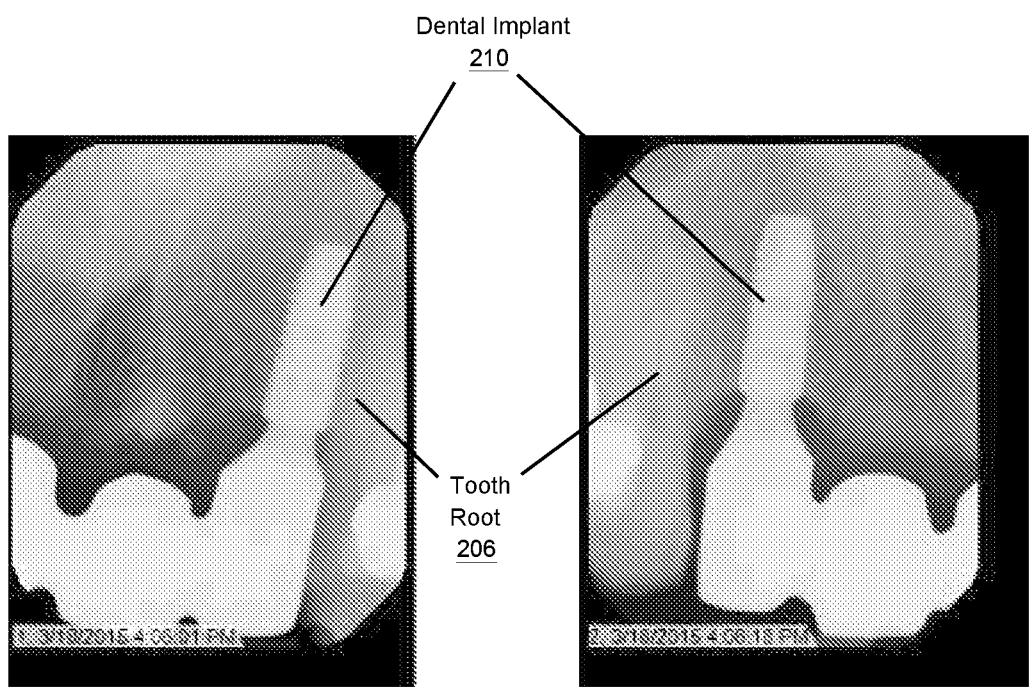

FIGS. 2A-2D illustrates example images from different orientations 200A-200D showing different installed components 208 for identification, in accordance with an embodiment of the present invention. As shown in FIGS. 2A and 2B, installed dental implant component 208 can be viewed from multiple orientations, e.g., angles, as installed in bone and/or tooth root 206. The radiographs of FIGS. 2A and 2B show different installed components in different environments, each environment may include various elements, including teeth 202 and dental restorations 204. As shown, these elements from different views may make identification of the installed components difficult and/or may interfere with the identification of such components. As discussed, embodiments of the present invention are configured to identify dental implants 208 as installed. For example, as shown in FIGS. 2C and 2D the same implant 210 may be imaged from two different orientations in different radiographs.

Figure 3:
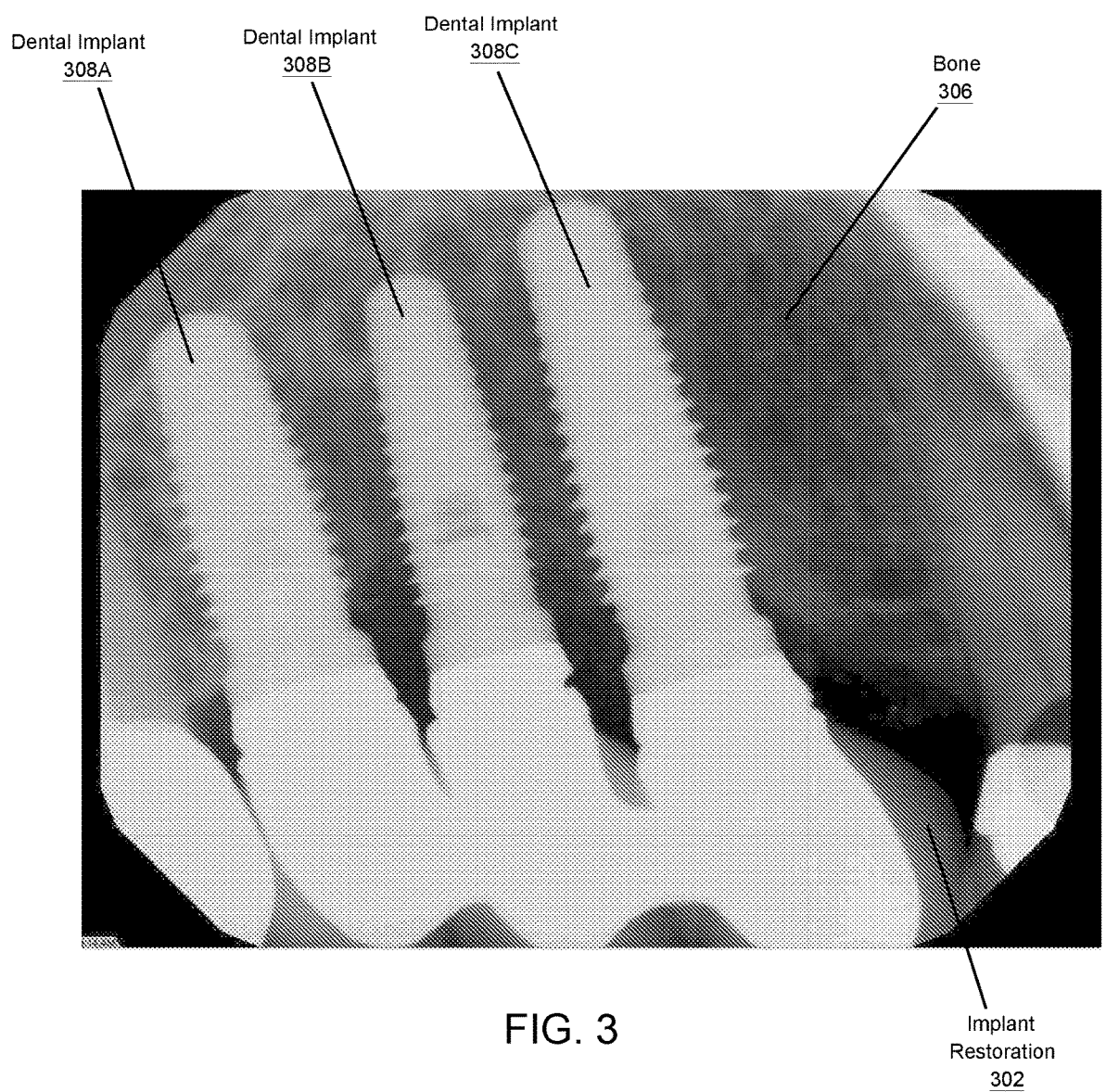
FIG. 3 illustrates an example image showing multiple installed components for identification, in accordance with an embodiment of the present invention.

FIG. 3 illustrates an example radiograph 300 showing multiple installed components 308A-308C, in accordance with an embodiment of the present invention. Similar to the imaging data of FIG. 2 described above, the imaging data of FIG. 3 may include a radiograph of a patient's mouth. The radiograph includes bone 306 and teeth 302 with a first implant 308A, second implant 308A, and third implant 308A (i.e., installed components) installed in three different teeth 302.

Figure 4:
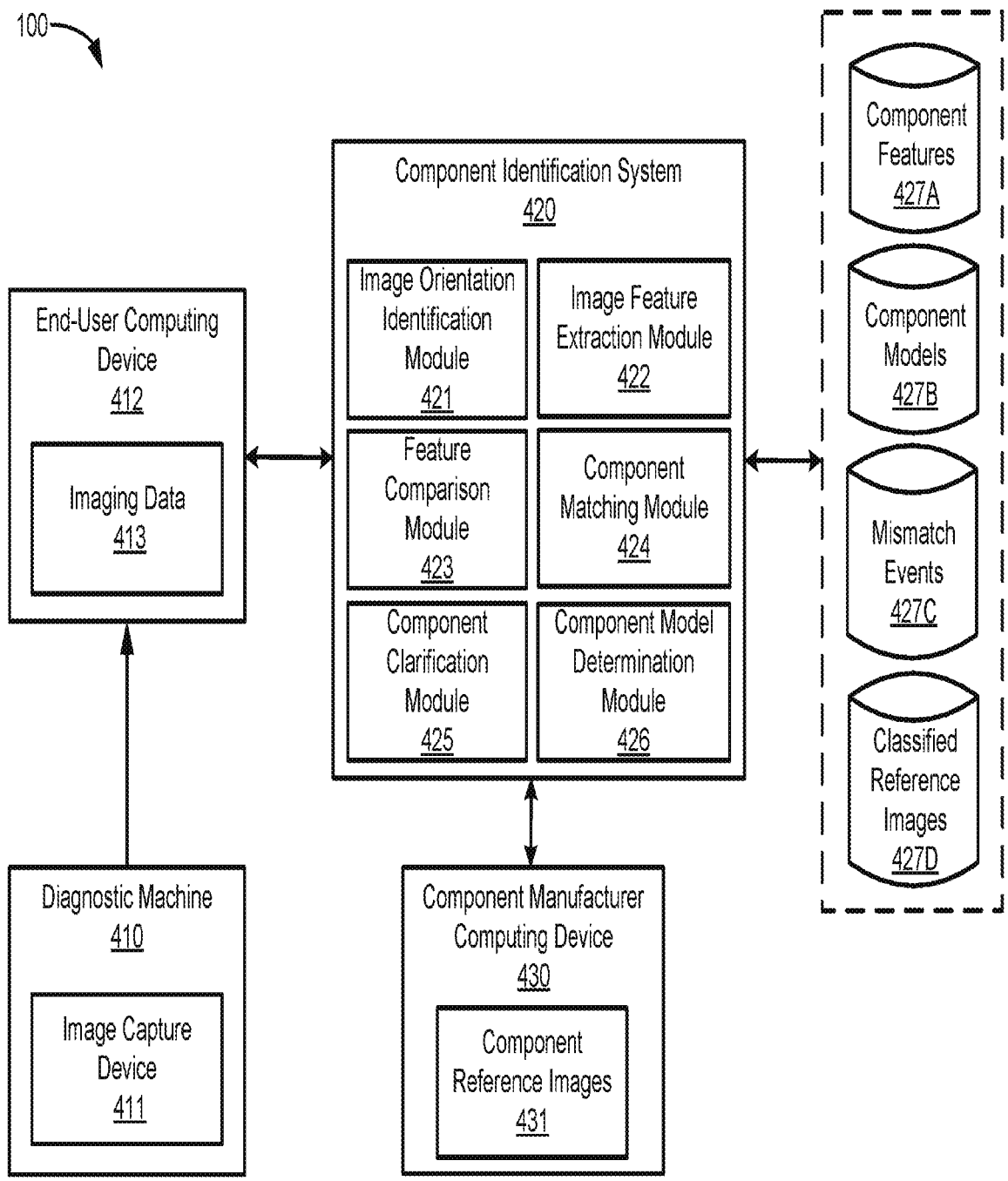
FIG. 4 is an exemplary block diagram of an implant identification system, in accordance with an embodiment of the present invention.

FIG. 4 is an exemplary block diagram of an implant identification system, in accordance with an embodiment of the present invention. FIG. 4 is an example of an environment 400 including a diagnostic machine 410, an end-user computing device 412, a component identification system 420, and a component manufacturer computing device 430. The various devices may be configured to communicate over one or more communication networks (not shown) that may be wired or wireless and may use any suitable communication protocol.

The diagnostic machine 410 may include any machine configured to obtain imaging data of an installed component. For example, the diagnostic machine may include an X-ray machine that generates two dimensional radiographs of installed components within a patient's mouth (or other area). The diagnostic machine may include an image capture device 411 that is configured to take the radiograph imaging data. The image capture component 411 may implement any technology to identify installed components and/or implants that may not be visible to the human eye. For example, the image capture module 411 may implement radiography techniques to obtain images including, for example, X-ray imaging, a panoramic radiograph, a magnetic resonance imaging (MRI) scan, a computerized axial tomography (CAT) scan, a cone-beam computed tomography (CBCT) scan, etc. The imaging data 413 may include at least one superimposed 2D representation of all the internal structures that are captured by the imaging method. Thus, two dimensional imaging data showing internal structure that is otherwise not visible by the human eye may be captured by the imaging data. Once the radiographic imaging data is obtained, the imaging data 413 may be transmitted to the end-user computing device 412.

The end-user computing device 412 may be associated with a doctor, surgeon, hospital and/or other provider that may be interested in identifying components from images. The end-user computing device 410 may include any device that is configured to obtain imaging data of an installed component, communicate the imaging data over one or more communication networks, and receive component identification results over the one or more communication networks. For example, the end-user computing device may include a desktop, laptop, smart phone, tablet, smart watch, VR headset, digital glasses, and/or any other suitable devices that may be associated with one or more providers. In some embodiments, the end-user computing device may be configured to obtain imaging data of installed components from the diagnostic machine 410. For example, the imaging data may include a radiographic image of a portion of a patient's body. The imaging data 413 may be obtained from a diagnostic machine 410 that is configured to obtain the imaging data using an image capture component 411. In some embodiments, the end-user computing device 412 may be part of the diagnostic machine 410 and/or may be a separate computer that receives the imaging data captured by the diagnostic machine. The end-user computing device 412 is configured to communicate with the component identification system 420 to send the imaging data 413 and receive component information associated with one or more matching components in response to submitting the imaging data.

The component identification system 420 may include any computing system that is configured to receive imaging data including installed components from an end-user computing device, identify the installed component associated with the imaging data, and provide component information to the end-user computing device. The component identification system 420 may include an image orientation identification module 421, an image feature extraction module 422, a feature comparison module 423, a component matching module 424, a component clarification module 425, and a component model determination module 426.

The image orientation identification module 421 may be configured to receive imaging data and process the imaging data to identify an orientation of the installed component. For example, for a dental implant, the reference point for the orientation may be defined as the orientation of the dental implant in relation to the imaging data. For instance, the z axis may be along the depth direction of the implant, the x axis and y axis may be the width of the dental implant in either horizontal direction along the z axis of the dental implant. Alternatively, and/or additionally, in some embodiments, the orientation may be defined according to a reference point associated with the patient. For example, the orientation may be defined according to a reference plane that is defined for each type of component that is attempting to be identified. For instance, if the type of component being identified is a dental implant, a predetermined reference plane may be defined according to a center point of the jaw. As such, an orientation of the imaging data may be defined on an x, y, and z axis according to the difference between the center point of the jaw and the point of view of the radiograph. Any suitable predefined orientation for the reference x, y, and z axis may be used as long as the reference plane and corresponding determined orientations are defined consistently across the various reference images and component models. The image orientation identification module 421 may identify the orientation and reference frame in which the imaging data (also referred to as an image) was taken and use the orientation information to process the image and normalize the image against a reference plane to allow for image comparison and feature identification. In some embodiments, the image orientation identification module may be configured to normalize the imaging data once the orientation of the installed component is identified. In such embodiments, the image matching process may use normalized reference images to compare and match images. In other embodiments, the identified orientation may be used and image matching processing may be performed without normalizing the imaging data to a reference orientation. In some embodiments, the image orientation information may also be used to limit the number of images that are later used to compare and calculate a similarity score in order to increase the speed and efficient use of system resources as will be described in further detail below. For example, the determined orientation information may be used to identify and/or select a subset of a plurality of reference images in each component model and/or a reference set of reference images stored for all reference components. As such, fewer images are required to be analyzed, leading to more efficient image comparison processing.

The image feature extraction module 422 may be configured to process the imaging data to identify a plurality of features associated with the installed component. In some embodiments, the image feature extraction module 422 may be configured with image processing technology to identify the installed component within the imaging data and measure the various sizes, length, shape, and/or other features associated with the installed component. For example, the image feature extraction module 422 may identify the installed component within the image by looking for contrast in brightness within the image that corresponds to the installed component. As shown in FIGS. 2A-2D and 3, the installed component is significantly brighter than the background and the bone and other tissue represented within the radiograph. In some embodiments, an image vector map may be defined across the image and the vector map information may be used to identify and extract particular features associated with the installed component. For example, site specific markers on the implant threads, grooves, platform, and apex of the component may be identified and used to measure features associated with the installed component in the image.

In some embodiments, the image feature extraction module 422 may be configured to identify features of the installed component including a length of the component, a width of the component, a type of interface of the component, a type of flange of the component, presence of microthreading on a coronal end of the component, a presence of a collar on the coronal end of the component, a type of taper of a body of the component, a presence of threading on the body of the component, a type of the threading on the body of the component, a presence of grooves in the body of the component, a shape of an apex end of the component, a presence of an open apex end of the component, a shape of the body of the component, a shape of apertures within the apex end of the component, a presence of a chamber in the apex end of the component, and a presence of grooves within the apex end of the component. Additional features may also be identified by the image feature extraction module 422 including the number of installed components within the image, a depth within the substrate and/or flesh that the component is installed, information associated with a type of flesh and/or area of the flesh that the component is installed in, information associated with a type of biological entity (e.g., human, animal, type of animal, etc.) in which the component is installed, information associated with an age of the biological entity, and/or any other information that may be gleaned from the image.

A feature comparison module 423 may be configured to identifying a plurality of reference components associated with the plurality of features from a plurality of registered reference components. The feature comparison module 423 may obtain the features extracted by the image feature extraction module 422 and search a data store of features associated with a plurality of reference components for those components that match one or more of the features extracted from the image. As such, the feature extraction module 423 may obtain a list of one or more components that may be associated with the features extracted from the image. For example, the feature comparison module 423 may obtain a list of features associated with an installed component and may search a component features data store for components having those features. For instance, the list of features extracted from the image may include the component having a length of 44-46 mm, a width of 4-8 mm, a flat apex, and a threaded body. The feature comparison module may determine that 5 components have those matching features and may return identifiers associated with those features.

A component matching module 424 may be configured to identify the similarity between the image and the reference components associated with the extracted features. The component matching module 424 may use any number of different comparison techniques to identify matching components to the image. For example, the component matching module 424 may generate a relevance score for each of the reference components identified as matching the identified features and use the relevance score to identify the most likely and/or matching reference component to the installed component. In some embodiments, the component matching module 424 may perform an image comparison to determine a relevance score for each of the returned components based on a similarity between the image and a plurality of reference images in a component model of each of the plurality of reference components. For example, in some embodiments, the component matching module 424 may compare the extracted features from the imaging data to a three dimensional mapping of each reference component to identify the fit of the installed component to the component model. The relevance score may be determined based on the "fit" or the differences between the extracted features and the three dimensional mapping of the component from the component model. In some embodiments, the three dimensional map may include a variety of two dimensional reference images of the component taken from a variety of orientations and distances. In such embodiments, the relevance score may be determined similarly by comparing the differences between the identified features from the image and one or more of the plurality of reference images associated with the component model.

Additionally and/or alternatively, in some embodiments, the component matching module 424 may determine the relevance scores by comparing the image to each of the plurality of reference images in the component model for each of the plurality of reference components and identifying a closest matching reference image of the plurality of reference images in the component model for each of the plurality of reference components. Accordingly, the component matching module 424 may use image matching to identify one of a plurality of reference images that match the orientation, placement, and/or angle of the installed implant from a plurality of reference images of the reference component. The component matching module 424 may compare only a portion of the imaging data (e.g., the installed component) to a portion of the reference image (e.g., the reference component within the reference image). In some embodiments, the component matching module 424 may compare the entirety and/or multiple portions of the images to determine a closest matching reference image.

Once the closest matching image has been determined, the component matching module 424 may calculate a similarity metric between the installed component in the imaging data and the reference component in the closest matching reference image for each of the plurality of reference components. Accordingly, the component matching module 424 may identify a reference image having the most similar orientation and placement to the present imaging data and use that closest matching reference image to identify the similarity between the installed component and the reference component. Any suitable method of calculating the similarity metric may be used including mapping of points of interest from the installed component to the reference component of the reference image, identification of features to compare, and/or any other suitable method.

Additionally and/or alternatively, in some embodiments, the component matching module 424 may train a component classifier algorithm using computer learning algorithms and a reference set of classified reference images to identify an appropriate component based on the image similarity between the image and the classified reference images. Accordingly, in some embodiments, the component matching module 424 may classify the image based on a size and shape of the installed component in the image using the trained component classifier algorithm. The component matching module 424 may determine the relevance scores for each of the reference components based on the results for the component classifier algorithm where the component classifier algorithm may be configured to provide a fit and/or a match score for each of the reference components associated with the features.

Once the relevance scores are calculated for each of the reference components, the component matching module 424 may compare each relevance score to a threshold relevance score to identify those relevance scores that indicate a likely match. It may be difficult to identify a particular component for some images because the orientation of the image and the corresponding installed component may be difficult to identify distinguishable features. As such, in some embodiments, multiple components may have relatively high relevance scores based on the image matching. Thus, the component matching module 424 may compare each of the relevance scores to a threshold relevance score to identify those components that have a good chance of being a match (relevance score above the threshold) versus those components that are likely not a match (relevance score below the threshold). For example, based on the image matching, the 5 components that had features matching the image, only 2 may have relevance scores over a threshold relevance score. Accordingly, the component matching module 424 may remove the other three reference component matches from a set of matching reference components.

In some embodiments, the component matching module 424 may generate a probability of a match based on the remaining relevance scores and the differences between the set of remaining relevance scores. For example, the component matching module 424 may track the results of previous matching processes to identify those image matches that resulted in positive and negative matches. Thus, the component matching module 424 may know that where there are two relevance scores over the threshold and the difference between the relevance scores is a particular amount or percentage of the relevance scores, the probability of a match may be generated. For instance, if the relevance scores are 0.3 and 0.5, meaning the difference in relevance scores is 0.2 and/or that the highest relevance score is 66% larger than another relevance score, the probability of the component with the higher relevance score being a correct match is 71%. Thus, the component matching module 424 may provide a probability of a match to allow a user to better understand and put into context the relevance scores generated by the image matching processes. Accordingly, the component matching module 424 may return the two possible matches and the corresponding probabilities of each component being a match (e.g., 71% and 29%). The end-user may be able to use the indication of the level of confidence in the match to either provide additional images to determine the correct match and/or rely on the probabilities to move forward with the match.

A component clarification module 425 may be configured to provide information that would increase the probability of one of the components being a confirmed match with the end-user. For example, where there is a 71% and a 29% probability of each component being a match, the component clarification module may provide the results of the match as well as provide further information to the end-user regarding other steps that may be performed to confirm a correct match. For instance, the component clarification module 425 may compare features of the matching components and identify differences (i.e., differentiating features) between the two possible matching components. The component clarification module 425 may have a set of instructions that are stored with each type of difference between various components to provide those instructions to an end-user to allow them to either provide the appropriate information to distinguish the components and/or allow the end-user to rule out one of the options based on that information.

Figure 6A:
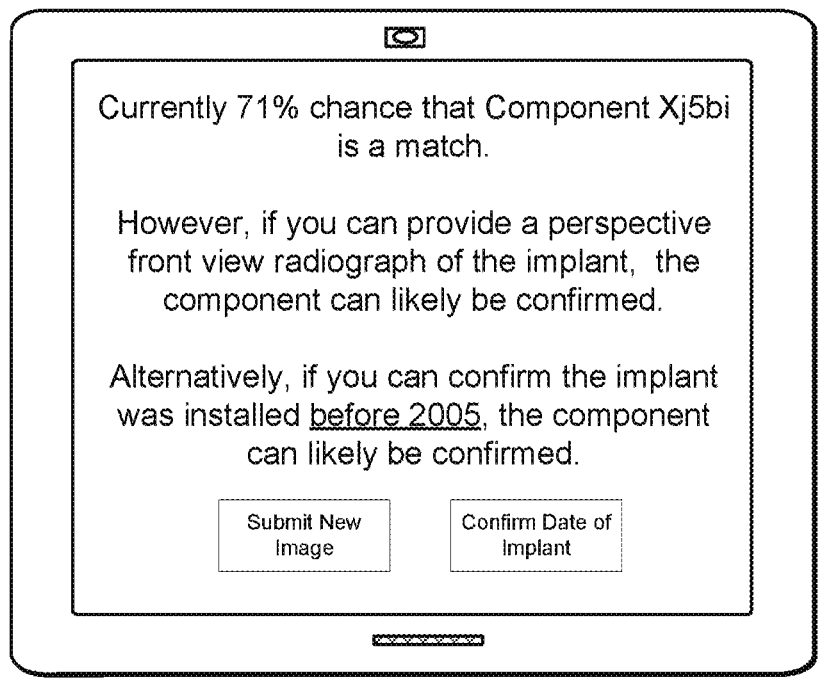
FIGS. 6A-6B illustrate exemplary interactions with an end-user computing device during a clarification process for identifying an implant, in accordance with an embodiment of the present invention.

FIG. 6A shows one example of the results of the component clarification module identifying differentiating features and providing information to the end-user regarding how those differentiating features may be identified. As shown in FIG. 6A, the component clarification module may identify that one of the components has a 71% chance of being the correct match and identify additional images that may allow the component identification system 420 to identify the matching component with a certainty. For instance, the component clarification module may identify that between the two potentially matching reference components, one of the reference components has a distinguishing feature on the front that can be seen from a perspective front view of the implant that was not previously shown in the image. As such, the component clarification module may instruct the end-user to provide that view in order to increase the certainty of the match. Moreover, the component clarification module may determine that one of the components was not available before a certain date and may provide timing, implant area, and/or other constraints that may eliminate one of the two matching reference components to obtain a certainty match. For example, the component clarification module may provide a time constraint to the end-user asking if they can confirm the component was installed before the year 2005 because one of the two components was not available at that time. Accordingly, if the end-user selects one of the two clarification options, the component clarification module may use the submitted information to either perform an additional matching and relevance score determination and/or eliminate one of the two matching components based on the provided timing constraint by the end-user. Any other suitable information that confirms and/or clarifies the differences between the multiple matching components may be implemented by the component clarification module to obtain a confirmation of the type of installed component.

Once one or more components are confirmed as being a match, the component identification system 420 may provide a component identifier and component information for each of the at least one matching reference component to the end-user computing device. The component identification system 420 may provide any suitable information that may be useful to an end-user. For example, the component information may include instructions for removing the component, tool information to be used with the component, a make and model of the component, warnings and/or instructions for working with the component, and/or any other information that may be used by a surgeon, dentist, health-provider and/or any other end-user associated with the installed component. The type of information may be dependent on the type of component being identified and matched but any information stored at the component identification system 420 and/or by an associated third party may be provided in response to the image query.

A component model determination module 426 may be configured to generate and/or determine the reference component models that are used by the component identification system 420 to perform the image comparison and matching as described herein. For example, the component model determination model may be configured to build classifying models for identifying matching components, classify different reference images associated with different components, and/or train one or more component models.

In some embodiments, the component model determination module 426 may be configured to build three dimensional component models of each component. The three dimensional models may include a variety of two dimensional images from a variety of different orientations that allow for matching to images of any orientation of the components. Accordingly, the component model determination module 426 may be configured to build a model that can be used to compare an installed component in imaging data to the model based on an orientation, distance/size, and/or placement of the installed component.

In some embodiments, the component model determination module 426 may be configured to train a component model using a machine learning algorithm applied to a plurality of reference images of the plurality of reference components previously classified as being associated with at least one of the plurality of reference components. Any suitable machine learning algorithm may be used and the reference images of the plurality of reference components may be large enough for the machine learning algorithm to identify visual differences between the various reference components and generate clustering of visually distinguishable features within the various reference images associated with the various reference components.

In some embodiments, the component model determination module 426 may build a component model for each reference component by including a reference set of images of the reference component from a variety of orientations, angles, distances, etc. Accordingly, the component model determination module may build a reference library of reference images for each component that show how that component may appear when installed and use the reference library of reference images to identify similar components.

Figure 6B:
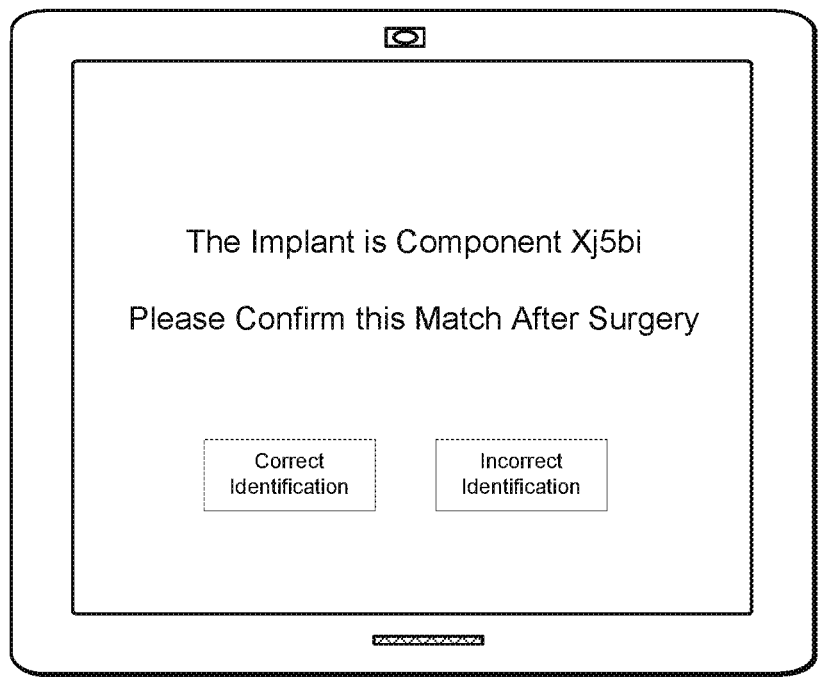

In some embodiments, the component model determination module 426 may be configured to receive feedback regarding the results of provided matches and incorporate the feedback into the component models that are generated and used by the component identification system 420. For example, the component model determination module 426 may receive a selection of one of the at least one matching reference component from the end-user computing device and update the component model associated with the matching reference component to include the image as a reference image of the reference component. Thus, the reference images that make up a component model may be updated with positive feedback and over time, the accuracy of the models may increase as additional reference images are added to deal with a variety of different orientations, angles, distances, and/or image qualities. FIG. 6B shows one example of an end-user device interface asking the end-user for feedback regarding the match of the component that may be used to further build the component model and/or image repository for a component. For example, the interface may request confirmation from the service provider as to whether the matched component is correct after an interaction (e.g., surgery, dental restoration, maintenance, or repair, etc.) with the patient.

The component identification system 420 may be configured to communicate with a variety of information data stores 427A-427D to perform the identification of the components based on the received image. For example, the component identification system 420 may have access to a component features data store 427A, component models data store 427B, mismatch events data store 427C, and classified reference images data store 427D. The data stores may include any suitable data storage and/or computer-readable memory to allow for storage and access of data stored therein.

The component features data store 427A may include a plurality of reference components and their corresponding classified features associated with each reference component. The component features data store 427A may be searchable such that the component identification system 420 may provide a set of features and receive a set of matching reference components that match at least one of or all of the provided features. The component features data store 427A may be built by the component identification system 420 and/or may be imported from component manufacturers or another third party collecting component feature information. The features may include, for example, a length of the component, a width of the component, a type of interface of the component, a type of flange of the component, presence of micro-threading on a coronal end of the component, presence of a collar on the coronal end of the component, a type of taper of a body of the component, presence of threading on the body of the component, a type of the threading on the body of the component, presence of grooves in the body of the component, a shape of an apex end of the component, presence of an open apex end of the component, a shape of the body of the component, a shape of apertures within the apex end of the component, presence of a chamber in the apex end of the component, and presence grooves within the apex end of the component.

The component models data store 427B may include one or more component models that may be used in matching and/or comparing imaging data to identify matching components. As described above, different types of component models may be implemented and thus, the type of information stored for each component model may be different depending on the implementation of the component models. The component models may be obtainable by the component matching module to compare imaging date to the one or more models and/or applying the imaging data to the component model for identifying a matching reference component.

The mismatch events data store 427C may include any information that allows the component identification system 420 to obtain feedback regarding mismatching results. As described previously, in some embodiments, feedback may be received from the end-user regarding the matching probabilities and/or quality of the match that was provided and the information may be stored and/or updated and incorporated into the component models. Accordingly, the mismatch events data may include a log of mismatched components and the features that caused the mismatch so that a list of clarifying questions and/or other information may be learned over time to ensure fewer mismatches in the future.

The classified reference images data store 427D may include any reference images that have been previously classified and confirmed as being associated with a particular reference component. For example, an end-user may confirm a matching reference component provided by the system and the component identification system 420 may store the imaging data that was received during the component identification process to further train the machine learning models and/or to build into the component model associated with the matched reference component. Accordingly, the component identification system 420 may learn from confirmed matches and use the query imaging data to further improve the models generated and/or determined by the component identification system 420.

The component manufacturer computing device 430 may include any computing device that is capable of providing component reference images associated with one or more components to the component identification system 420. For example, the component manufacturer computing device may include a desktop computer that provides component reference images 431, component models, component features, and/or any other suitable information related to the reference components to the component identification system 420 for use in building component models, identifying features associated with each of the reference components, and/or identifying installed components from imaging data. The component reference images 431 may include images of the component in an uninstalled state or real-world examples of imaging data from installed components of the reference component. Each component manufacturer may have a separate component manufacturer computing device that provides the relevant reference images, models, and/or features list to the component identification system 420. In some embodiments, the component manufacturer computing device may include a third party library of reference components that may or may not be associated with a particular manufacturer.

Although embodiments may be described in reference to a component being a dental implant and in the medical field generally, any number of different types of components may be identified through similar component identification functionality. Accordingly, embodiments are not limited to use at hospitals or in medical related fields and one of ordinary skill may recognize that embodiments could be implemented for any number of different services that have needs for components to be identified.

Figure 5:
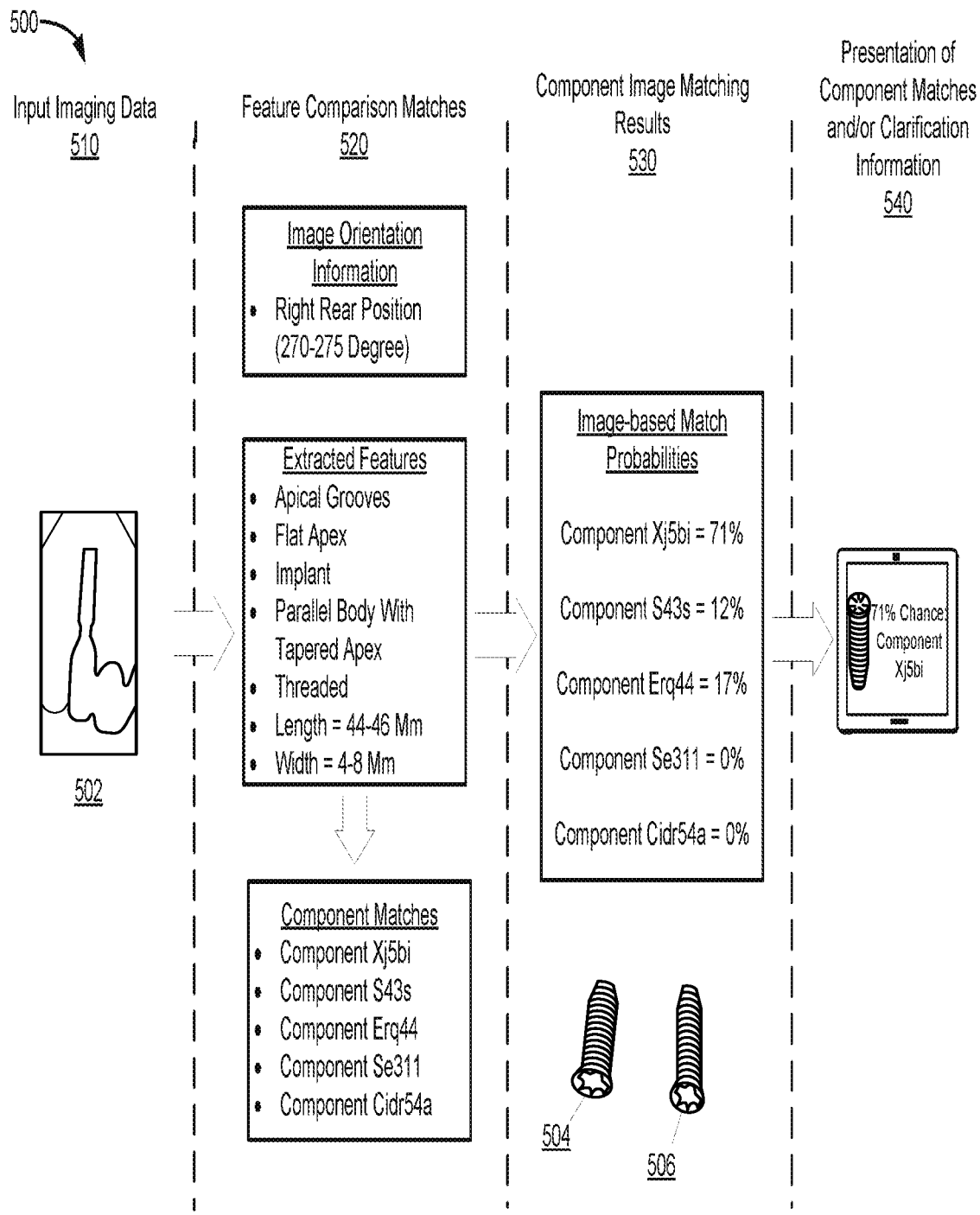
FIG. 5 is an exemplary flow diagram of a method of identifying implants from an image, in accordance with an embodiment of the present invention.

FIG. 5 is an exemplary flow diagram of a method of identifying implants from an image, in accordance with an embodiment of the present invention. At step 510, the component identification system 420 receives input imaging data including an installed component. For example, the imaging data may include a radiograph of an installed implant. In some embodiments, the imaging data may be enhanced by the system if the imaging data does not meet a predetermined quality level. Alternatively and/or additionally, in some embodiments, the imaging data may be enhanced regardless of the image quality. Digital image processing techniques may be applied to the imaging data to highlight the specific features, change the color and contrast between the background, tissue, and bone versus the implant component, and/or through any other suitable techniques to allow the implant identification system to optimize and/or increase the efficacy of the image matching. In some embodiments, the enhanced images may be saved as reference images and the reference component models may be enhanced similarly to ensure uniformity between images and models.

At step 520, the component identification system 420 processes the received image and performs feature comparison matches to identify reference components associated with the extracted features from the image. For example, the component identification system 420 may identify an orientation from the installed components of the image, extract a set of identifiable features of each installed component from the image, and identify reference component matches associated with the set of identifiable features. For instance, in this example, 5 reference components are identified as having the set of features identified from the imaging data. Note that depending on the orientation and quality of the received imaging data, different numbers of features may be extracted and/or identified which may influence the number of matching components that match the set of features.

At step 530, the component identification system 420 performs image matching processes for the identified component matches to identify component image matching results. For example, the component identification system 420 obtained the 5 matching components that shared the extracted features from the image and performed an image matching process on each of them using the associated component model for each of the matching components to calculate a probability of a match to the installed component. As can be seen in FIG. 5, some of the components matched well and others matched poorly leading to a 0% chance of matching. For example, the input imaging data of the installed component 502 may be compared to the captured images of the stand-alone reference component views 504, 506 having similar orientations to the input imaging data 502. As can be seen, when the input imaging data is compared to the reference component model for each reference component, the images with similar features will have a higher image matching score than those that do not have the same features. As such, the reference component image matching may return accurate identification of those reference components matching the input imaging data by comparing images from similar orientations and viewpoints as the input data. Although a reference component model of a stand-alone reference component is shown for reference components 504, 506, in some embodiments, the reference images may be other radiographs of components captured at similar orientations and distances as the input images.

Additionally, in some embodiments, the identified orientation may be used to limit the number of reference component images that are used to perform the image matching process for the identified component matches. For example, embodiments may limit the images that are used from a reference component model to those that are within a range of orientations associated with the identified orientation. Accordingly, the system resources may be saved and the process speed may be increased by limiting the number of images that are compared during the image matching process.

At step 540, the component identification system 420 provides the matching component information to the end-user computing device 412. Each of the matching probabilities and/or relevance scores identified by the components image matching results may be compared to a threshold relevance score to identify those that have a good chance of a being a match and removing those that do not have a good chance of matching. As such, the component provided as a match is the reference component with the highest match probability but the chance of matching is also provided to the end-user computing device 412. FIG. 6A shows another example of the component information that may be provided to the end-user to allow the end-user to clarify the match and provide information that will lead to a confirmation of the matching component.

Figure 7:
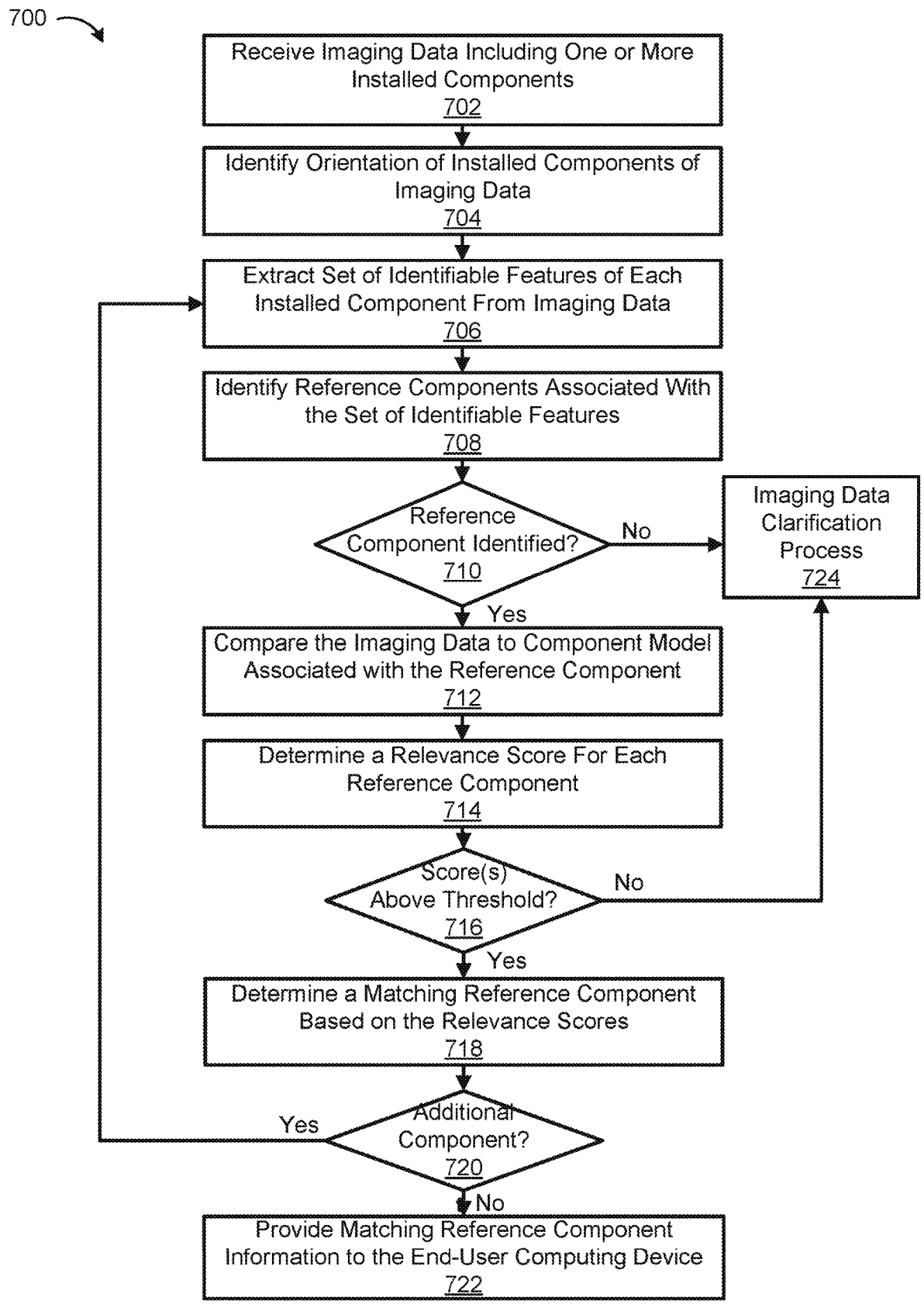
FIG. 7 is an exemplary flow diagram of a method for identifying an implant from an image, in accordance with an embodiment of the present invention.

FIG. 7 is an exemplary flow diagram of a method for identifying an installed component in an image query, in accordance with an embodiment of the present invention. At step 702, the component identification system 420 receives imaging data including one or more installed components. The imaging data may show the installed component from any orientation, placement, and/or size or distance.

At step 704, the component identification system 420 identifies an orientation and distance of the imaging date by analyzing the installed component of the image. As described above, the orientation may be defined according to any suitable reference point but should be consistently applied across all reference images and component models.

At step 706, the component identification system 420 extracts a set of identifiable features of each installed component from the image. The set of identifiable features may change based on the orientation of the installed component and quality of the imaging data.

At step 708, the component identification system 420 identifies reference components associated with the set of identifiable features. For example, the component identification system 420 may search a component feature data store 427A for reference components matching the set of features extracted from the imaging data. A set of reference components may be returned that can be analyzed using image matching to identify the reference component associated with the installed component.

At step 710, the component identification system 420 determines whether a reference component was identified. For example, in some embodiments, insufficient features may be identified and/or the features that are identified are not differentiating such that every component meets the extracted features. If no reference components are identified there may be a problem with the imaging data and an image clarification process may be initiated to provide feedback to the end-user regarding what information can be provided to improve the matching process.

At step 712, if a reference component was identified, the component identification system 420 compares the image to a component model associated with the reference component. As described above, there are a variety of different comparison methods that may be implemented to obtain matching reference components using component models. For example, relevance scores may be determined based on image comparison methods, application of a trained classifier model, and/or by mapping the imaging data to a three dimensional model of the reference component. Either way, a similarity between the installed component in the imaging data and the component in the reference images may be determined for each of the identified relevant reference components.

At step 714, the component identification system 420 determines a relevance score for each reference component. As described above, the method of determining the relevance score may differ based on the image matching processing being implemented. Further, in some embodiments, the relevance scores may incorporate information outside of the image matching including manufacturing date, market availability of the component, information related to the entity from which the imaging data was obtained (e.g., patient), and/or any other suitable information.

At step 716, the component identification system 420 determines whether any of the set of reference components is over a threshold relevance score. For example, if a relevance score is too small such that the chance is minor that the component is in fact the correct match but because the imaging data found some commonality, the relevance score may be discarded. This may limit false positives where the imaging data uses similarity between most reference components to identify similarities that are not meaningful for actual matching of components. For example, all of the reference components have somewhat similar body shape and/or placement within an image but those similarities do not help differentiate between different components. Accordingly, a threshold relevance score that is above the relevance score generated for these common attributes amongst the various components may be identified so that those components that share only these common attributes may be removed from the set of matching components.

At step 718, if at least one of the relevance scores was over a threshold, the component identification system 420 determines one or more matching reference components based on the relevance scores. Multiple components may be selected as matching reference components in some embodiments or, in other embodiments, only the highest matching component may be provided.

At step 720, the component identification system 420 determines whether there were multiple installed components identified in the image. If multiple components were identified, the process returns to step 706 for the next installed component and the process is repeated for each installed component until each installed component is identified.

At step 722, if there are no additional components remaining to be identified, the component identification system 420 provides the matching reference component information to the end-user computing device.

At step 724, the component identification system 420 performs an image clarification process that informs the end-user to provide additional and/or different images with different orientations. The image clarification process may be initiated in response to a blurry and/or poor image that does not provide sufficient distinguishable features to allow the identification of matching components. FIG. 6A shows one example of an interface showing the information that may be provided during an image clarification process in order to obtain additional data to allow for a more certain identification of the installed component. The method using the component identification system may also include automatically online ordering of replacement implants after and responsive to identifying a matching piece of hardware. As will be understood by those skilled in the art, by identifying a matching piece of hardware by use of the component identification system, indicators, signals, data, or other techniques may be used to complete an online request to order one or more replacement implants. Verification may occur before or after initiating an online order to make sure that the match is correct and/or that the online order being automatically placed or otherwise placed electronically is correct.

Figure 8:
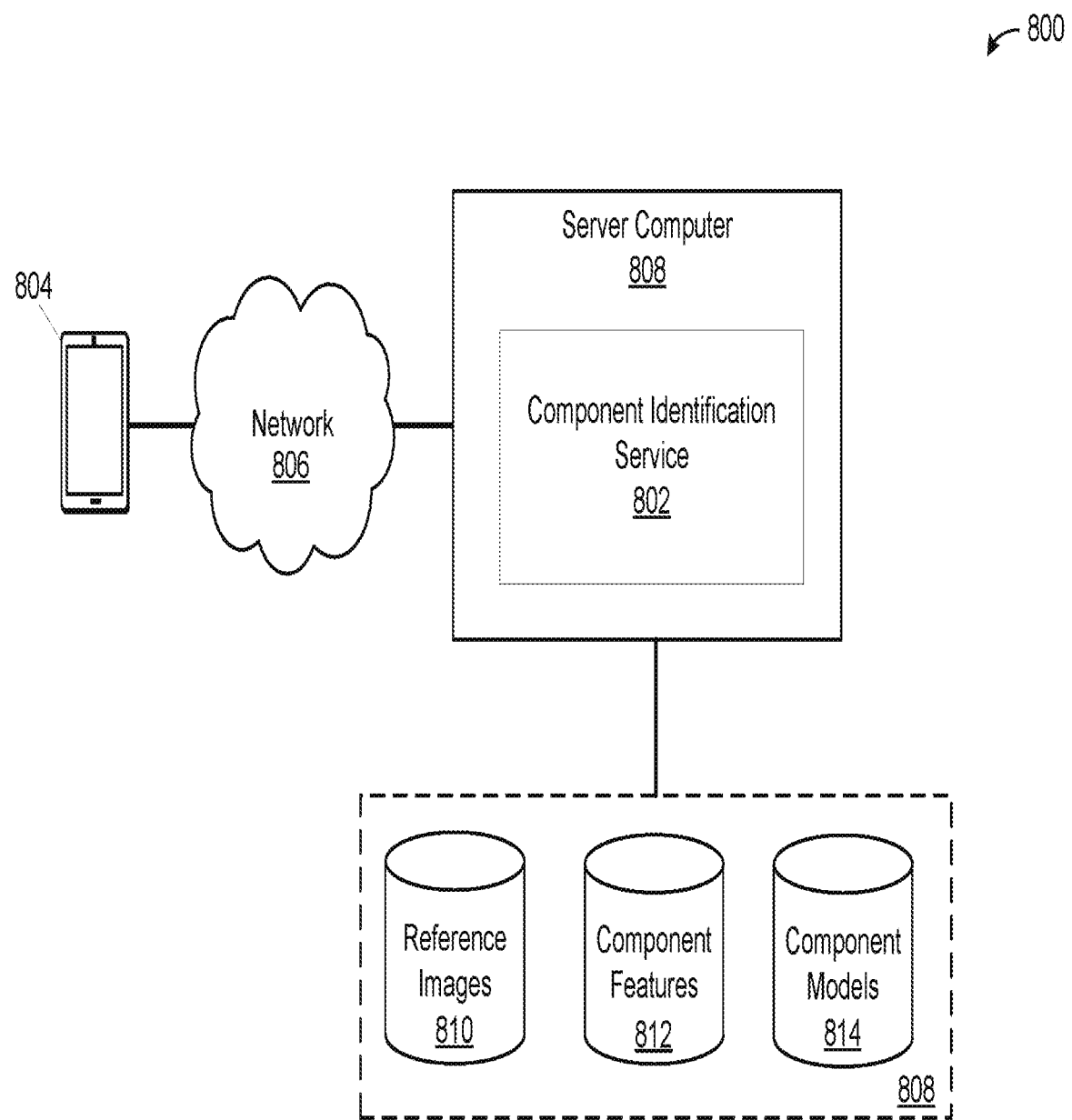
FIG. 8 is a schematic diagram of an example implant identification system, in accordance with various embodiments.

FIG. 8 shows a component identification environment 800, in accordance with various embodiments. As shown in FIG. 8, the component identification service 802 may be configured to receive imaging data from a computing device 804. The component identification service 802 may be hosted on one or more computers and/or servers or any combination thereof. For example, the component identification service 802 may be hosted by server computer 808. The computing device 804 may include, but are not limited to, end-user devices including laptop or desktop computers, mobile phones, tablets, etc., as well as component manufacturing computing devices 820, diagnostic machines (not shown), and/or other electronic communication devices.

Data received by the component identification service 802 can be stored in data store 808. Data store 808 can include one or more data stores, such as databases, object storage systems and services, cloud-based storage services, and other data stores. For example, various data stores may be implemented on a non-transitory storage medium accessible to component identification service 802, such as reference images data store 810, component features data store 812, and component models data store 814. Data stores 808 can be local to electronic record management system 802, or remote and accessible over a network, such as those networks discussed above or a storage-area network or other networked storage system.

The server computer 808 can connect to various devices through network 806. The network 806 can include any network configured to send and/or receive data communications using various communication protocols, such as AppleTalk™, transmission control protocol/Internet protocol (TCP/IP), Internet packet exchange (IPX), systems network architecture (SNA), etc. In some embodiments, the network can include local area networks (LAN), such as Ethernet, Token-Ring or other LANs. The network 806 can include a wide-area network and/or the Internet. In some embodiments, the network 806 can include VPNs (virtual private networks), PSTNs (a public switched telephone networks), infra-red networks, or any wireless network, including networks implementing the IEEE 802.11 family of standards, Bluetooth®, Bluetooth® Low Energy, NFC and/or any other wireless protocol. In various embodiments, the network can include a mobile network, such as a mobile telephone network, cellular network, satellite network, or other mobile network. In some embodiments, the network may each include a combination of networks described herein or other networks as are known to one of ordinary skill in the art.

Although a particular implementation of environment 800 is shown in FIG. 8, this is for illustration purposes only and not intended to be limited. In some embodiments, environment 800 may include fewer or more components, as may be recognized by one or ordinary skill in the art. In some embodiments, server computer 802, end-user computing device 804, or any other computing device described herein can be implemented using a computer system which may include, but is not limited to mobile devices, tablet computing devices, wearable devices, personal or laptop computers, or other devices or systems described herein. The computer system may include an I/O device subsystem, a display device subsystem, and a storage subsystem including one or more computer readable storage media. The subsystems may also include a memory subsystem, a communication subsystem, and a processing subsystem. The bus facilitates communication between the various subsystems. Examples of such bus systems may include a local bus, parallel bus, serial bus, bus network, and/or multiple bus systems coordinated by a bus controller. The bus may implement various standards such as Parallel ATA, serial ATA, Industry Standard Architecture (ISA) bus, Extended ISA (EISA) bus, MicroChannel Architecture (MCA) bus, Peripheral Component Interconnect (PCI) bus, or any other architecture or standard as is known in the art.

In some embodiments, the computing system may include an I/O device subsystem. The I/O subsystem may include various input and/or output devices or interfaces for communicating with such devices. Such devices may include, without limitation, a touch screen or other touch-sensitive input device, a keyboard, a mouse, a trackball, a motion sensor or other movement-based gesture recognition device, a scroll wheel, a click wheel, a dial, a button, a switch, audio recognition devices configured to receive voice commands, microphones, image capture based devices such as eye activity monitors configured to recognize commands based on eye movement or blinking, and other types of input devices. I/O device subsystem may also include identification or authentication devices, such as fingerprint scanners, voiceprint scanners, iris scanners, or other biometric sensors or detectors. In various embodiments, I/O device subsystem may include audio output devices, such as speakers, media players, or other output devices.

The computing system may include a display device subsystem. The display device subsystem may include one or more lights, such as an one or more light emitting diodes (LEDs), LED arrays, a liquid crystal display (LCD) or plasma display or other flat-screen display, a touch screen, a head-mounted display or other wearable display device, a projection device, a cathode ray tube (CRT), and any other display technology configured to visually convey information. The computing system may include a storage subsystem including various computer readable storage media, such as hard disk drives, solid state drives (including RAM-based and/or flash-based SSDs), or other storage devices. In various embodiments, computer readable storage media can be configured to store software, including programs, code, or other instructions, that is executable by a processor to provide functionality described herein. In some embodiments, storage system may include various data stores or repositories or interface with various data stores or repositories that store data used with embodiments described herein. Such data stores may include, databases, object storage systems and services, cloud-based storage systems and services, file systems, distributed data stores, and any other data storage system or service. In some embodiments, storage system can include a media reader, card reader, or other storage interface to communicate with one or more external and/or removable storage devices. In various embodiments, computer readable storage media can include any appropriate storage medium or combination of storage media. For example, computer readable storage media can include, but is not limited to, any one or more of random access memory (RAM), read only memory (ROM), electronically erasable programmable ROM (EEPROM), flash memory or other memory technology, optical storage (e.g., CD-ROM, digital versatile disk (DVD), Blu-ray® disk or other optical storage device), magnetic storage (e.g., tape drives, cassettes, magnetic disk storage or other magnetic storage devices). In some embodiments, computer readable storage media can include data signals or any other medium through which data can be transmitted and/or received.

Memory subsystem can include various types of memory, including RAM, ROM, flash memory, or other memory. The memory can include SRAM (static RAM) or DRAM (dynamic RAM). In some embodiments, memory can include a BIOS (basic input/output system) or other firmware configured to manage initialization of various components during, e.g., startup. The memory can additionally include an operating system, such as macOS®, Windows®, Linux®, various UNIX® or UNIX- or Linux-based operating systems, or other operating systems.

The computing system can also include a communication subsystem configured to facilitate communication between system and various external computer systems and/or networks (such as the Internet, a local area network (LAN), a wide area network (WAN), a mobile network, or any other network). The communication subsystem can include hardware and/or software to enable communication over various wired (such as Ethernet or other wired communication technology) or wireless communication channels, such as radio transceivers to facilitate communication over wireless networks, mobile or cellular voice and/or data networks, Wi-Fi networks, or other wireless communication networks. Additionally, or alternatively, communication subsystem can include hardware and/or software components to communicate with satellite-based or ground-based location services, such as GPS (global positioning system). In some embodiments, the communication subsystem may include, or interface with, various hardware or software sensors. The sensors may be configured to provide continuous or and/or periodic data or data streams to a computer system through communication subsystem.

The processing system can include one or more processors or other devices operable to control computing system. The processing system can include central processing units (CPUs), graphical processing units (GPUs), application specific integrated circuits (ASICs), digital signal processors (DSPs) or any other generalized or specialized microprocessor or integrated circuit. Various processors within the processing system, may be used independently or in combination depending on application.

Various other configurations may also be used, with particular elements that are depicted as being implemented in hardware may instead be implemented in software, firmware, or a combination thereof. One of ordinary skill in the art will recognize various alternatives to the specific embodiments described herein.

The specification and figures describe particular embodiments which are provided for ease of description and illustration and are not intended to be restrictive. Embodiments may be implemented to be used in various environments without departing from the spirit and scope of the disclosure.

The use of the terms "a" and "an" and "the" and similar referents in the context of describing the disclosed embodiments (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the disclosure and does not pose a limitation on the scope of the disclosure unless otherwise claimed. No language in the specification should be construed as indicating any non-claimed element as essential to the practice of the disclosure.

Disjunctive language such as the phrase "at least one of X, Y, or Z," unless specifically stated otherwise, is intended to be understood within the context as used in general to present that an item, term, etc., may be either X, Y, or Z, or any combination thereof (e.g., X, Y, and/or Z). Thus, such disjunctive language is not generally intended to, and should not, imply that certain embodiments require at least one of X, at least one of Y, or at least one of Z to each be present.

This application is a U.S. National Phase Under 35 U.S.C. § 371 of International Application No. PCT/US17/67316, titled "METHODS AND SYSTEMS FOR IMPLANT IDENTIFICATION USING IMAGING DATA," filed Dec. 19, 2017, which is a PCT application claiming priority to and the benefit of U.S. Provisional Application No. 62/436,324, titled "METHODS AND SYSTEMS FOR IMPLANT IDENTIFICATION USING IMAGING DATA," filed Dec. 19, 2016, which is incorporated herein in its entirety by reference.

Preferred embodiments of this disclosure are described herein, including the best mode known to the inventors for carrying out the disclosure. Variations of those preferred embodiments may become apparent to those of ordinary skill in the art upon reading the foregoing description. The inventors expect skilled artisans to employ such variations as appropriate and the inventors intend for the disclosure to be practiced otherwise than as specifically described herein. Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context.

What is claimed is:

1. A method comprising:
receiving, by a component identification system, imaging data from an end-user computing device, the imaging data including a single image of an installed component;
processing, by the component identification system, the imaging data to identify a plurality of features associated with the installed component;
identifying a plurality of reference components associated with the plurality of features from a plurality of registered reference components;
determining a plurality of relevance scores, each of the plurality of relevance scores being determined for one of the plurality of reference components, wherein each relevance score is based on a similarity between the imaging data and a plurality of reference images in a component model of each of the plurality of reference components, the determining the plurality of relevance scores including:
comparing the installed component of the imaging data to each of the plurality of reference images in the component model for each of the plurality of reference components,
identifying a closest matching reference image of the plurality of reference images in the component model for each of the plurality of reference components, and
calculating a similarity metric between the installed component of the imaging data and the reference component in the closest matching reference image for each of the plurality of reference components;
identifying at least one matching reference component by comparing each relevance score of the plurality of relevance scores to a threshold relevance score; and
providing, by the component identification system, a component identifier and component information for each of the at least one matching reference component to the end-user computing device.

2. The method of claim 1, wherein the plurality of features include at least two of a length of the component, a width of the component, a type of interface of the component, a type of flange of the component, presence of micro-threading on a coronal end of the component, presence of a collar on the coronal end of the component, a type of taper of a body of the component, presence of threading on the body of the component, a type of the threading on the body of the component, presence of grooves in the body of the component, a shape of an apex end of the component, presence of an open apex end of the component, a shape of the body of the component, a shape of apertures within the apex end of the component, presence of a chamber in the apex end of the component, and presence grooves within the apex end of the component.

3. The method of claim 1, wherein the plurality of reference images in each component model further comprises a plurality of reference images of the reference component from a plurality of orientations.

4. The method of claim 1, wherein the single image of the installed component is captured from a reference orientation and wherein the similarity between the imaging data and the plurality of reference images in the component model of each of the plurality of reference components is based on the reference orientation.

5. The method of claim 1, further comprising:
receiving a selection of one of the at least one matching reference component from the end-user computing device; and
updating the component model associated with the matching reference component to include the imaging data as a reference image of the reference component.

6. The method of claim 1, further comprising:
processing the imaging data to identify an orientation associated with the installed component of the imaging data; and
selecting a subset of the plurality of reference images in each component model associated with each reference component based on the orientation associated with the installed component of the imaging data.

7. The method of claim 1, wherein the component model associated with the reference component is determined by processing, using a machine learning algorithm, a plurality of reference images of the plurality of reference components previously classified as being associated with at least one of the plurality of reference components.

8. The method of claim 1, wherein the imaging data includes a radiograph of the installed component.

9. The method of claim 1, wherein providing the component identifier and the component information for each of the at least one matching reference component to the end-user computing device further comprises providing a probability of matching the installed component.

10. The method of claim 1, wherein each component model includes a plurality of reference images of a respective reference component to form a three dimensional model of the respective reference component.

11. The method of claim 1, wherein determining a plurality of relevance scores further comprises:
applying a component classifier algorithm to the imaging data, the classifier algorithm having been trained, using a machine learning algorithm, to classify the installed component in the imaging data based on a size, placement, and shape of the installed component in the imaging data using a plurality of classified reference images associated with the plurality of reference components; and
determining the relevance scores for each of the reference components based on the results for the component classifier algorithm.

12. A computing device comprising:
a processor; and
a computer-readable medium coupled to the processor, the computer-readable medium comprising code, executable by the processor, to cause the computing device to:
receive imaging data from an end-user computing device, the imaging data including a single image of an installed component;
process the imaging data to identify a plurality of features associated with the installed component;
identify a plurality of reference components associated with the plurality of features from a plurality of registered reference components;
determine a plurality of relevance scores, each of the plurality of relevance scores being determined for one of the plurality of reference components, wherein each relevance score is based on a similarity between the imaging data and a plurality of reference images in a component model of each of the plurality of reference components, the plurality of relevance scores being determined by comparing the installed component of the imaging data to each of the plurality of reference images in the component model for each of the plurality of reference components; identifying a closest matching reference image of the plurality of reference images in the component model for each of the plurality of reference components; and calculating a similarity metric between the installed component in the imaging data and the reference component in the closet matching reference image for each of the plurality of reference components;
identify at least one matching reference component by comparing each relevance score of the plurality of relevance scores to a threshold relevance score; and
provide a component identifier and component information for each of the at least one matching reference component to the end-user computing device.

13. The computing device of claim 12, wherein the computer-readable medium further comprises code, executable by the processor, to cause the computing device to:
receive a selection of one of the at least one matching reference component from the end-user computing device; and
update the component model associated with the matching reference component to include the imaging data as a reference image of the reference component.

14. The computing device of claim 12, wherein the single image of the installed component is captured from a reference orientation and wherein the similarity between the imaging data and the plurality of reference images in the component model of each of the plurality of reference components is based on the reference orientation.

15. A computing device comprising:
a processor; and
a computer-readable medium coupled to the processor, the computer-readable medium comprising code, executable by the processor, to cause the computing device to:
receive imaging data from an end-user computing device, the imaging data including a single image of an installed component;
process the imaging data to identify a plurality of features associated with the installed component;
identify a plurality of reference components associated with the plurality of features from a plurality of registered reference components;
determine a plurality of relevance scores, each of the plurality of relevance scores being determined for one of the plurality of reference components, wherein each relevance score is based on a similarity between the imaging data and a plurality of reference images in a component model of each of the plurality of reference components and the plurality of relevance scores being determined by applying a component classifier algorithm to the imaging data, the classifier algorithm having been trained, using a machine learning algorithm, to classify the installed component in the imaging data based on a size, placement, and shape of the installed component in the imaging data using a plurality of classified reference images associated with the plurality of reference components; and determining the relevance scores for each of the reference components based on the results for the component classifier algorithm;
identify at least one matching reference component by comparing each relevance score of the plurality of relevance scores to a threshold relevance score; and
provide a component identifier and component information for each of the at least one matching reference component to the end-user computing device.

16. A system comprising:
a component identification system configured to:
receive imaging data associated with an installed component from an end-user computing device, the imaging data including a single image of an installed component;
process the imaging data to identify a plurality of features associated with the installed component;
identify a plurality of reference components associated with the plurality of features from a plurality of registered reference components;
determine a plurality of relevance scores, each of the plurality of relevance scores being determined for one of the plurality of reference components, wherein each relevance score is based on a similarity between the imaging data and a plurality of reference images in a component model of each of the plurality of reference components, the plurality of relevance scores being determined by comparing the installed component of the imaging data to each of the plurality of reference images in the component model for each of the plurality of reference components; identifying a closest matching reference image of the plurality of reference images in the component model for each of the plurality of reference components; and calculating a similarity metric between the installed component in the imaging data and the reference component in the closest matching reference image for each of the plurality of reference components;

identify at least one matching reference component by comparing each relevance score of the plurality of relevance scores to a threshold relevance score; and transmit a component identifier and component information for each of the at least one matching reference component to the end-user computing device;

the end-user computing device configured to:

obtain the imaging data associated with the installed component;

transmit the imaging data to the component identification system;

receive the component identifier and component information for each of the at least one matching reference component from the component identification system; and display the component information to a user.

17. The system of claim 16, wherein the component identification system is further configured to:

receive a selection of one of the at least one matching reference component from the end-user computing device; and update the component model associated with the matching reference component to include the imaging data as a reference image of the reference component.

18. The system of claim 16, wherein the single image of the installed component is captured from a reference orientation, wherein the similarity between the imaging data and the plurality of reference images in the component model of each of the plurality of reference components is based on the reference orientation.

* * * * *